(12) United States Patent
Ren et al.

(10) Patent No.: US 7,253,289 B2
(45) Date of Patent: Aug. 7, 2007

(54) ONE-STEP PROCESS FOR THE PREPARATION OF HALIDE-FREE HYDROPHOBIC SALTS

(75) Inventors: Rex Xiaofeng Ren, Middletown, CT (US); Victor R. Koch, Lincoln, MA (US)

(73) Assignee: Covalent Associates, Inc., Woburn, MA (US)

( * ) Notice: Subject to any disclaimer, the term of this patent is extended or adjusted under 35 U.S.C. 154(b) by 506 days.

(21) Appl. No.: 10/250,801

(22) PCT Filed: Jan. 22, 2002

(86) PCT No.: PCT/US02/01766

§ 371 (c)(1),
(2), (4) Date: Jul. 9, 2003

(87) PCT Pub. No.: WO02/094883

PCT Pub. Date: Nov. 28, 2002

(65) Prior Publication Data

US 2004/0225131 A1    Nov. 11, 2004

(51) Int. Cl.
C07D 233/00    (2006.01)

(52) U.S. Cl. .................................. 548/335.1
(58) Field of Classification Search .............. 548/335.1
See application file for complete search history.

(56) References Cited

U.S. PATENT DOCUMENTS

| 5,182,405 | A | 1/1993 | Arduengo, III | 548/335.1 |
| 5,827,602 | A | 10/1998 | Koch et al. | 429/194 |
| 6,319,428 | B1 | 11/2001 | Michot et al. | 252/500 |
| 6,939,974 | B2 * | 9/2005 | Earle et al. | 548/347.1 |

FOREIGN PATENT DOCUMENTS

WO    WO 00/72956 A1    7/2000

OTHER PUBLICATIONS

Arduengo., 1993, CAS: 116:106289.*
P. Bonhôte, et al., "Hydrophobic, Highly Conductive Ambient-Temperature Molten Salts", 1996, American Chemical Society, pp. 1168-1178.
D. Morrison, et al., "Base-Promoted Reactions in Ionic Liquid Solvents. The Knoevenagel and Robinson Annulation Reactions", Tetrahedron Letters, 2001, pp. 6053-6055.
J. Huddleston, et al., "Characterization and Comparison of Hydrophilic and Hydrophobic Room Temperature Ionic Liquids Incorporating the Imidazolium Cation", Department of Chemistry, University of Alabama, Apr. 2001.
J. Wilkes, et al., "Air and Water Stable 1-Ethyl-3-Methylimidazolium Based Ionic Liquids", 1992, J. Chem. Soc., Chem. Commun., pp. 965-967.
H. Zhang, et al., "Free Radical Polymerization in Room Temperature Ionic Liquids", Polymer Reprints, 2001, pp. 583-584.
Alan McEwen, et al., "Electrochemical Properties of Imidazolium Salt Electrolytes for Electrochemical Capacitor Applications", Journal of the Electrochemical Society, 1999, pp. 1687-1695.

* cited by examiner

Primary Examiner—Rebecca Anderson
Assistant Examiner—Rei-tsang Shiao
(74) Attorney, Agent, or Firm—Weingarten, Schurgin, Gagnebin & Lebovici LLP (57) ABSTRACT

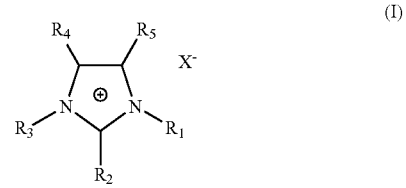

This invention describes a one pot, single-step process for the preparation of halide-free hydrophobic salts comprising polyalkylated imidazolium cations and various anions in accordance with the following structure, where $R^1$ and $R^3$ represent the either the same or different alkyl groups, and $R^2$, $R^4$, and $R_5$ represent either hydrogen atoms, or the same or different alkyl group substituents; X represents a polyatomic anion that is the conjugate base of an acid. By simply mixing aqueous formaldehyde with an alkyl amine such as methylanune, ethylamine, n-propyl oriso-propylamine, or n-butyl-, iso-butyl, or t-butylamine, or by mixing aqueous formaldehyde with two alkyl amines (preferably one being methylamine, ethylamine, n-propyl- or iso-propylamine, or n-butyl-, isobutyl, or t-butylamine) and another being n-propyl- or isopropylaine, or n-butyl-, isbutyl, or t-butylamine), an acid (such as hexafluorophosphoric acid, trifluoroacetic acid, pentafluoropropionic, heptafluorobutyric acid, or the free acid of a bis(perfluoroalkylsulfonyprnide or tris(perfluoroalkylsulfonyl)methide as the source of the anion) and aqueous glyoxal solution, the hydrophobic ionic salts or mixtures thereof thus formed may be conveniently separated directly from the aqueous byproduct layer. Like the single cation hydrophobic salts, these mixed hydrophobic ionic liquids are non-flammable and manifest no detectable vapor pressure up to their decomposition temperature of greater than 300° C. We have also discovered that, surprisingly, ternary mixtures of dialkylated ionic liquids manifest higher ionic conductivities than a single ionic liquid of the mixture alone. This property benefits electrochemical power source applications such as batteries and capacitors. Furthermore, we have discovered that ternary mixtures of dialkylated ionic liquids absorb microwave radiation more efficiently than a single ionic liquid of the mixture alone. This property benefits microwave-induced synthetic reactions. Such physical and chemical properties make it possible to employ inexpensive mixtures of polyalkylated imidazolium cations in an advantageous manner as thermal transfer fluids, high temperature lubricants, and plasticizers, and as solvents in the areas of electrochemistry, synthetic chemistry, catalysis, and separations chemistry.

18 Claims, 2 Drawing Sheets

ONE-STEP PROCESS FOR THE PREPARATION OF HALIDE-FREE HYDROPHOBIC SALTS

This application is a 371 of PCT/US02/01766 filed on Jan. 22, 2002.

CROSS REFERENCE TO RELATED APPLICATIONS

This application claims the priority of U.S. Provisional Application No. 60/262,661 filed Jan. 22, 2001 entitled ONE-STEP PROCESS FOR PREPARATION OF HYDROPHOBIC IONIC LIQUIDS, the whole of which is incorporated by reference herein.

FIELD OF THE INVENTION

This invention relates to a simple, one-step method of preparing halide-free hydrophobic salts comprising polyalkylated imidazolium cations and mixtures thereof using inexpensive reactants. Such polyalkylated imidazolium cations, when paired with polyatoniic anions for charge balance, offer tremendous potential in applications such as thermal transfer fluids, high temperature lubricants, and plasticizers, and as solvents in the areas of electrochemistry, synthetic chemistry, catalysis, and separations chemistry.

BACKGROUND OF THE INVENTION

Hydrophobic salts are a class of materials comprising electronically delocalized organic cations and polyatomic organic or inorganic anions. These salts, which typically possess melting points of less than 175° C., and more particularly, below 150° C., may also be liquid at room temperature and below.

In the 1940s Hurley and Wier first disclosed the preparation and use of ionic salts, which were fluid at room temperature, comprising the electronically delocalized N-alkylpyridinium cation and haloaluniinate inorganic anions in a series of U.S. Pat. (Nos. 2,446,331, 2,446,339, and 2,446,350). However, the practical utility of these haloaluminate-based pyridinium salts is severely compromised by their extremely high reactivity with trace amounts of water leading to the liberation of heat and toxic gases.

In the 1990s, air and water stable salts comprising the electronically delocalized 1,3-dialkylimidazolium cation and non-haloaluminate anions, e.g. $BF_4^-$ and $PF_6^-$ were prepared by Wilkes and coworkers (*J Chem. Soc. Chem. Comm.* 965 [1992]). However, these salts, because the alkyl groups on the imidazolium cation possessed less than three carbon atoms, have a significant solubility in water and may not be described as "hydrophobic". Ellis describes (WO 9618459) a process for making ionic liquids by reacting a solution of a lead salt of an anion desired in the ionic liquid with 1,3-dialkylimidazolium halide salts, and separating the lead halide precipitate from an aqueous solution of the hydrophilic ionic liquid product. Finally, in U.S. Pat. No. 5,182,405 Arduengo describes a one-step process for the preparation of salts comprising 1,3-disubstituted imidazolium cations and the conjugate base of an acid. These salts, which are highly hydrophilic, are prepared via reaction of an alpha-dicarbonyl compound, an aldehyde (in toluene), an amine, and an acid comprising hydrogen halides, sulfric acid, or phosphoric acid.

The multi-step preparation of the more technologically useful hydrophobic salts comprising 1,3-dialkylimidazolium cations and the bis[trifluoromethylsulfonyl]imide anion was disclosed in U.S. Pat. No. 5,683,832 and in *Inorg. Chem.* 1168 (1996). U.S. Pat. No. 5,827,602 describes a multi-step reaction route leading to a broad spectrum of air and water stable hydrophobic salts comprising 1,3-dialkylimidazolium cations coupled with non-Lewis acid containing polyatomic anions possessing a van der Waals volume of greater than 100 $Å^3$.

However, all of the known procedures for preparation of hydrophobic salts minimally involve a two-step reaction sequence starting with an expensive 1-alkyllimidazole followed by alkylation by an alkyl halide. In addition to the high cost of the alkylimidazole, halide impurities (such as $Cl^-$, $Br^-$, and $I^-$) from alkyl halide starting materials are both difficult and time consuming to remove. The purification step employing a silver reagent to produce halide-free hydrophobic salts is very expensive and unsuitable as an industrial process. Therefore, a need exists to improve the process for the preparation of ionic salts that are both hydrophobic and halide-free. The ability to inexpensively produce industrial quantities of such salts will enable the introduction of these technologically useful materials into a host of cost-sensitive chemical and engineering applications.

BRIEF SUMMARY OF THE INVENTION

One object of this invention is to describe a novel process capable of producing hydrophobic salts inexpensively and halide-free. Another object of this invention is to produce mixtures of low melting hydrophobic salts inexpensively and halide-free. A further object of this invention is to demonstrate that mixtures of hydrophobic salts possess hitherto unrealized advantages that make such mixtures more useful for various applications than a single hydrophobic salt alone.

This invention describes a one pot, single-step process for the preparation of halide-free hydrophobic salts comprising polyalkylated imidazolium cations and various anions in accordance with the following structure, where $R_1$ and $R_3$ represent the either the same or different alkyl groups, and $R_2$, $R_4$, and $R_5$ represent either hydrogen atoms, or the same or different alkyl group substituents; $X^-$ represents a polyatomic anion that is the conjugate base of an acid.

By simply mixing aqueous formaldehyde with an alkyl amine such as methylamine, ethylamine, n-propyl- or iso-propylamine, or n-butyl-, iso-butyl, or t-butylamine, or by mixing aqueous formaldehyde with two alkyl amines (preferably one being methylamine, ethylamine, n-propyl- or iso-propylamine, or n-butyl-, iso-butyl, or t-butylamine) and another being n-propyl- or iso-propylamine, or n-butyl-, iso-butyl, or t-butylamine), an acid (such as hexafluorophosphoric acid, trifluoroacetic acid, pentafluoropropionic, heptafluorobutyric acid, trifluorosulfonic acid, or the free acid of a bis(perfluoroalkylsulfonyl)imide or tris(perfluoroalkylsulfonyl)methide as the source of the anion) and aqueous glyoxal solution, the hydrophobic salt thus formed may be conveniently separated directly from the aqueous byproduct layer.

Like the single cation hydrophobic salts, these mixed hydrophobic ionic liquids are non-flammable and manifest no detectable vapor pressure up to their decomposition temperature of greater than 300° C. We have also discovered that, surprisingly, ternary mixtures of dialkylated ionic liquids manifest higher ionic conductivities than a single ionic liquid of the mixture alone. This property benefits electrochemical power source applications such as batteries and capacitors. Furthermore, we have discovered that ternary mixtures of dialkylated ionic liquids absorb microwave radiation more efficiently than a single ionic liquid of the mixture alone. This property benefits microwave-induced synthetic reactions. Such physical and chemical properties make it possible to employ inexpensive mixtures of polyalkylated imidazolium cations in an advantageous manner as thermal transfer fluids, high temperature lubricants, and plasticizers, and as solvents in the areas of electrochemistry, synthetic chemistry, catalysis, and separations chemistry.

DETAILED DESCRIPTION OF THE INVENTION

Hydrophobic ionic salts based on polyalkylated imidazolium cations offer tremendous potential in applications such as thermal transfer fluids, high temperature lubricants, and plasticizers, and as solvents in the areas of electrochemistry, synthetic chemistry, catalysis, and separations chemistry. Huddleston and coworkers (Green Chemistry, 3, 156 [2001]) have recently identified hydrophobic salts and hydrophobic ionic liquids as possessing superior physical and chemical properties over hydrophilic ionic liquids in respect to separations chemistry. Organic annulation reactions were found by Morrison and coworkers (Tet. Lett., 42, 6053 [2001]) to proceed with excellent yields in a recyclable hydrophobic ionic liquid solvent. Zhang and coworkers (Polymer Preprints, 42, 583 [2001]) have found that free-radical polymerization reactions conducted in hydrophobic ionic liquids achieved higher molecular weights than those conducted in conventional organic solvents. McEwen and coworkers (J. Electrochem. Soc., 146, 1687 [1999]) have reported on the superiority of hydrophobic polyalkylated imidazolium salts as electrolytes for electrochemical double layer capacitors.

We have discovered that, surprisingly, ternary mixtures of dialkylated ionic liquids manifest higher ionic conductivities than a single ionic liquid of the mixture alone. Higher ionic conductivities allow an electrochemical power source, such as a battery or capacitor, to deliver more power and also to enable low temperature applications. We have also discovered that ternary mixtures of dialkylated ionic liquids absorb microwave radiation more efficiently than a single ionic liquid of the mixture alone. In particular, we find that an inexpensive 2:1:1 mixture of hydrophobic 1,3-dialkylated imidazolium hexafluorophosphates A, B, and C shown below reaches temperatures in excess of 150° C. in a matter of seconds. This property benefits microwave-induced synthetic reactions by reducing reaction times.

Applications relying on hydrophobic ionic salts would greatly benefit from a simple, inexpensive synthetic route to these novel materials. Hydrophobic ionic salts have previously been synthesized by a multi-step route relying on imidazole, alkylated imidazoles, and alkyl halide starting materials. Starting materials based on the imidazole ring are intrinsically expensive, and the use of alkyl halides in the reaction scheme results in Cl$^-$, Br$^-$, and I$^-$ byproducts that require extensive purification to eliminate. This adds significantly to the overall cost of the desired hydrophobic ionic salts.

The present invention provides a method for the convenient and inexpensive preparation of halide-free hydrophobic salts comprising one or more polyalkylated imidzolium cations and various polyatomic organic or inorganic anions. While Arduengo in U.S. Pat. No. 5,182,405 teaches a similar one-step route to imidazolium salts, it must be pointed out that such imidazolium salts are extremely hydrophilic in nature, and more difficult to purify than the hydrophobic ionic salts. The term "hydrophilic salt" is intended to mean a salt that is highly soluble in water. The term "hydrophobic salt" is intended to mean a salt that possesses very limited, if any, solubility in water. Some of the hydrophobic ionic salts may be termed ionic liquids. The term "ionic liquid" is intended to mean liquids that are comprised entirely of ions, and when in the neat form at a pressure of 1 atmosphere have a melting point of 150° C. or less.

We have developed a simple, one-step synthesis of the hydrophobic ionic salts shown below, where the $R_1$ and $R_3$ substituents of the polyalkylated imidazolium cation are $C_{1-20}$ alkyl groups, where "$C_{1-20}$ alkyl" is intended to mean a linear, cyclic, or branched hydrocarbon group having from 1 to 20 carbon atoms, such as methyl, ethyl, n-propyl, iso-propyl, cyclopropyl, n-butyl, sec-butyl, t-butyl group, cyclobutyl, pentyl, cyclopentyl, hexadecyl, heptadecyl, octadecyl, or nonadecyl. The $R_2$, $R_4$, and $R_5$ substituents represent either hydrogen atoms, or the same $C_{1-20}$ alkyl group substituents as defined for $R_1$ and $R_3$ above.

The counter ion "X" refers to either polyatomic inorganic or polyatomic organic anions that are the conjugate base of an acid "HX". Illustrative examples of such anions are $PF_6^-$, $AsF_6^-$, $SbF_6^-$, $C_nF_{2n+1}CO_2^-$, $C_nF_{2n+1}SO_3^-$, where n=1 to 10 carbon atoms in either straight or branched chains, $(C_nF_{2n+1}SO_2)_2N^-$, $(C_nF_{2n+1}SO_2)_3C^-$, where n=1 to 5 carbon atoms in either straight or branched chains, and $(C_nF_{2n+1})PF_5^-$, $(C_nF_{2n+1})_2PF_4^-$, $(C_nF_{2n+1})_3PF_3^-$, and $(C_nF_{2n+1})_4PF_2^-$, where n=1 to 5 carbon atoms in either straight or branched chains.

Hydrophobic polyalkylated imidazolium salts are obtained in one step from inexpensive and commercially available aldehydes, alkylamines, α-dicarbonyl compounds, glyoxal, and acids (HX) comprising polyatomic anions (X$^-$).

Aldehydes comprising either hydrogen or alkyl group substituents of from 1–10 carbon atoms are preferred. Pre- ferred alkylamines possess from 1–10 carbon atoms. When two or more amines are employed in the process, it is preferred that at least one amine comprise from 4–10 carbon atoms. α-Dicarbonyl compounds useful in the process preferably comprise either hydrogen and/or alkyl group substituents of from 1–10 carbon atoms.

Acids (HX) must comprise polyatomic counterions ($X^-$) and are limited to those counterions that result in hydrophobic rather than hydrophilic ionic salts. Preferred acids are $HPF_6$, $CF_3CO_2H$, $CF_3SO_3H$, $(CF_3SO_2)_2NH$, $(CF_3SO_2)_3CH$, and $(CF_3)_2PF_4H$.

The one-step process to halide-free hydrophobic ionic salts can be carried out between from about −20° C. to about 150° C., and most preferably between 0° C. to 75° C., preferably with stirring. Reaction times may vary from 1 to 72 hours depending upon the reaction temperature and more typically from 2 to 24 hours.

The hydrophobic ionic salts typically form as a solid precipitate, or as two liquid phases in the reaction vessel: a bottom layer comprising the hydrophobic ionic liquid (or ionic liquid mixture) immiscible with water, and an aqueous top layer. The desired reaction products may be easily separated from the undesired reaction byproducts by common means, for example by filtration in the case of solid products or decantation in the case of liquid products. It is the hydrophobic nature of the ionic salts of this invention that allows them to be readily obtained in high purity thus precluding the expense incurred by the need for extensive purification.

It has been discovered in this invention that salts composed of a mixture of three 1,3-dialkylimidazolium cations (i.e., $R_1 \neq R_3$,) and an anion, or of certain symmetrical 1,3-dialkylimidazolium cations, such as 1,3-di-n-propylimidazolium or 1,3-di-n-butylimidazolium (i.e., $R_1 = R_3$ ) and a suitable anion are hydrophobic ionic liquids at ambient temperature. The mixture of compounds can be represented by the following general structures, where $R_1$ and $R_3$ are alkyl radicals comprising a different number of carbon atoms, preferably $R_1$ being a methyl, ethyl, n-propyl, iso-propyl, n-butyl, sec-butyl, or t-butyl group and $R_3$ being a n-propyl, iso-propyl, n-butyl, sec-butyl, or t-butyl group, and $R_2$, $R_4$, and $R_5$ represent either hydrogen atoms, or the same or different alkyl group substituents as in $R_1$ and $R_3$. The mixture of imidazolium salts has a preferable ratio of A:B:C=2:1:1. By using a slightly higher proportion of n-propyl- or iso-propylamine, or n-butyl-, iso-butyl-, or t-butylamine, hydrophobic ionic liquids having a higher ratio of A and C can be produced. In cases where $R_1$ and $R_3$ are identical, they should preferably be n-propyl, iso-propyl, n-butyl, iso-butyl, or t-butyl groups. The counter ion "X" refers to either polyatomic inorganic or polyatomic organic anions that are the conjugate base of an acid "HX". Illustrative examples of such anions are $PF_6^-$, $AsF_6^-$, $SbF_6^-$, $C_nF_{2n+1}CO_2^-$, $C_nF_{2n+1}SO_3^-$, where n=1 to 10 carbon atoms in either straight or branched chains, $(C_nF_{2n+1}SO_2)_2N^-$, $(C_nF_{2n+1}SO_2)_3C^-$, where n=1 to 5 carbon atoms in either straight or branched chains, and $(C_nF_{2n+1})PF_5^-$, $(C_nF_{2n+1})_2PF_4^-$, $(C_nF_{2n+1})_3PF_3^-$, and $(C_nF_{2n+1})_4PF_2^-$, where n=1 to 5 carbon atoms in either straight or branched chains.

The following examples describe the preparation of hydrophobic salts according to this invention, as well as some of their physical and chemical properties that make them suitable for use in a broad spectrum of chemical and engineering applications. These examples are intended to further illustrate, but not limit, the invention.

EXAMPLE 1

Preparation of 1,3-Diethylimidazolium Hexafluorophosphate

Aqueous formaldehyde (15 ml of 37 wt % formaldehyde; 0.20 mol) was magnetically stirred in a 250 ml Erlenmeyer flask immersed in an ice bath. Aqueous ethylamine (32 ml of 70 wt % ethylamine; 0.40 mol) was added in drops to the cold formaldehyde. The solution was stirred 15 minutes and aqueous hexafluorophosphoric acid (30 ml of 60 wt % $HPF_6$; 0.20 mol) was added in small portions from a plastic syringe. A white precipitate formed during the addition, but re-dissolved to give a clear solution, which was stirred ~15 minutes before aqueous glyoxal (23 ml of 40 wt % glyoxal; 0.20 mol) was added drop-wise. The solution was stirred overnight, during which time the ice bath warmed to room temperature. A white precipitate formed. The mixture was stirred approximately another 30 hours at room temperature and was chilled in the refrigerator. The precipitate was collected by suction filtration, washed with cold water, and dried under vacuum at room temperature to give 21.4 g (79 mmol; 40%) of crude product, mp 70–72 ° C. Re-crystallization from methanol/diethyl ether afforded 16.8 g (62 mmol; 31%) of analytically pure material, mp 71–73 ° C.
IR (KBr) 3178, 3120, 1568, 1167, 843 $cm^{-1}$
$^1H$ NMR ($CD_3CN$) 8.44 (s, 1, $H_2$), 7.39 (d, 2, $H_4$, $H_5$), 4.16 (q, 4), 1.46 (t, 6) ppm
Anal. Calcd for $C_7H_{13}F_6N_2P$: C, 31.12; H, 4.86; N, 10.37. Found: C, 31.36; H, 4.83; N, 10.40.

EXAMPLE 2

Preparation of 1,3-Diethylimidazolium Hexafluoroarsenate

Aqueous ethylamine (32 ml of 70 wt % ethylamine; 0.40 mol) was added in drops to ice-cold, magnetically stirred aqueous formaldehyde (15 ml of 37 wt % formaldehyde; 0.20 mol) in a 250 ml Erlenmeyer flask immersed in an ice bath. Aqueous hexafluoroarsenic acid (59 g of 65 wt % $AsF_6H$; 0.20 mol) was added in drops, causing the separation of a white precipitate. The mixture was stirred 10 minutes before the addition of aqueous glyoxal (23 ml of 40 wt % glyoxal; 0.20 mol). The mixture was stirred overnight while the ice bath warmed to room temperature spontaneously. The two-phase reaction mixture consisted of an upper aqueous phase and a golden-yellow, viscous liquid. In the process of decanting the supernatant aqueous layer, the lower viscous liquid phase crystallized exothermically. The crystalline product was collected by suction filtration and washed with water. The product was dissolved in warm methanol and re-crystallized by addition of diethyl ether. The white crystalline product amounted to 42.14 g (134 mmol; 67%), mp 61–62° C.

IR (KBr) 3176, 3120, 1568, 1165, 848, 756, 696 cm$^{-1}$ $^1$H NMR (CD$_3$CN) 8.44 (s, 1, H$_2$), 7.39 (d, 2, H$_4$, H$_5$), 4.16 (q, 4), 1.46 (t, 6) ppm

EXAMPLE 3

Preparation of 1,3,4-Trimethylimidazolium Hexafluorophosphate

Aqueous methylamine (35 ml of 40 wt % methylamine; 0.40 mol) was added in drops to ice-cold, magnetically stirred aqueous formaldehyde (15 ml of 37 wt % formaldehyde; 0.20 mol) in a 250 ml Erlenmeyer flask immersed in an ice bath. After 10 minutes, aqueous hexafluorophosphoric acid (30 ml of 60 wt % HPF$_6$; 0.20 mol) was added in small portions from a plastic syringe. Finally, aqueous pyruvic aldehyde (33 ml of 40 wt % pyruvic aldehyde; 0.20 mol) was added in drops from a pipet. The reaction solution took on the yellow color of the pyruvic aldehyde. The solution was stirred while the ice bath was allowed to warm spontaneously. Within a few hours, a precipitate had formed and the color of the mixture had darkened. The mixture was stirred overnight at room temperature, by which time the mixture was dark red and contained a considerable proportion of solid. The precipitate was collected by suction filtration, washed with cold water, and filtered giving ~30 g of crude product. The crude product was dissolved in warm methanol (~100 ml), the solution was filtered, and the filtrate was allowed to cool. Crystals formed on standing overnight. The crystals were collected, washed with diethyl ether and dried under vacuum at room temperature. The yield was 21.76 g (85 mmol; 42%) of pale yellow crystals, mp 84–86° C.

IR (KBr) 3186, 3157, 3128, 1616, 1587, 1456, 1169, 850 cm$^{-1}$ $^1$H NMR (CD$_3$CN) 8.26 (s, 1, H$_2$), 7.07 (s, 1, H$_5$), 3.76 (s, 3), 3.68 (s, 3), 2.25 (d, 3) ppm Anal. Calcd for C$_6$H$_{11}$F$_6$N$_2$P: C, 28.13; H, 4.34; N, 10.94. Found: C, 28.35; H, 4.24; N, 10.93.

EXAMPLE 4

Preparation of 1,2,3,4-Tetramethylimidazolium Hexafluorophosphate

Aqueous methylamine (35 ml of 40 w/o methylamine; 0.40 mol) was added in a drop wise fashion to an ice-cold, magnetically stirred solution of acetaldehyde (12 ml; 0.20 mol) in 350 ml of water in a 500 ml Erlenmeyer flask in an ice bath. Aqueous hexafluorophosphoric acid (30 ml of 60 wt % HPF$_6$; 0.20 mol) was added slowly in small portions from a plastic syringe. Aqueous pyruvic aldehyde (33 ml of 40 wt % pyruvic aldehyde; 0.20 mol) was then added drop wise from a pipet. The solution was stirred overnight while the ice bath was allowed to warm spontaneously. The precipitate, which formed overnight was collected by suction filtration and washed with cold water. The crude product was re-crystallized from methanol to give 11.46 g (42 mmol; 21%) of 1,2,3,4-tetramethylimidazolium hexafluorophosphate as white crystals, mp 151–153° C.

IR (KBr) 3145, 2970, 1630, 1554, 1446, 1209, 847, 787 cm$^{-1}$ $^1$H NMR (CD$_3$CN) 6.97 (d, 1, H$_5$), 3.65 (s, 3), 3.55 (s, 3), 2.47 (s, 3), 2.23 (d, 3) ppm Anal. Calcd for C$_7$H$_{13}$F$_6$N$_2$P: C, 31.12; H, 4.86; N, 10.37. Found: C, 31.37; H, 4.91; N, 10.47.

EXAMPLE 5

Preparation of 1,3,4,5-Tetramethylimidazolium Hexafluorophosphate

Aqueous methylamine (35 ml of 40 wt % methylamine; 0.40 mol) was added in a drop wise manner to ice-cold, magnetically stirred aqueous formaldehyde (15 ml of 37 wt % formaldehyde; 0.20 mol) in a 250 ml Erlenmeyer flask in an ice bath. Aqueous hexafluorophosphoric acid (30 ml of 60 wt % HPF$_6$; 0.20 mol) was added in small portions from a plastic syringe, followed by drop wise addition of 2,3-butanedione (17.6 ml; 17.3 g; 0.20 mol). The reaction solution became yellow and viscous; it was stirred overnight while the ice bath warmed to room temperature. The mixture was chilled in the refrigerator. The precipitate was collected by suction filtration, washed with cold water, and dried under vacuum at room temperature to give 27.0 g (100 mmol; 50%) of crude product, mp 151–155° C. Re-crystallization from methanol afforded analytically pure material (23.0 g; 85 mmol; 43%), mp 156–158° C.

IR (KBr) 3190, 3128, 1585, 1454, 1213, 843 cm$^{-1}$ $^1$H NMR (CD$_3$CN) 8.22 (s, 1, H$_2$), 3.66 (s, 6), 2.19 (s, 6) ppm Anal. Calcd for C$_7$H$_{13}$F$_6$N$_2$P: C, 31.12; H, 4.86; N, 10.37. Found: C, 31.39; H, 4.94; N, 10.44.

EXAMPLE 6

Preparation of 1,2,3,4,5-Pentamethylnimdazolium Hexafluorophosphate

Aqueous methylamine (36 ml of 40 wt % methylamine; 0.42 mol) was added in a drop wise fashion to a cold, magnetically stirred solution of acetaldehyde (12 ml; 9.4 g; 0.21 mol) in water (~350 ml) in a 500 ml Erlenmeyer flask in an ice bath. The solution was stirred for 10 minutes and aqueous hexafluorophosphoric acid (30 ml of 60 wt % HPF$_6$; 0.20 mol) was slowly added from a plastic syringe. The solution was stirred 10 minutes before 2,3-butanedione (18 ml; 17.7 g; 0.21 mol) was added drop wise. The solution took on a pale yellow color and within 30 minutes, a precipitate formed. The mixture was stirred for two days at room temperature. The precipitate was collected by suction filtration, washed with water, and allowed to air dry. The crude product amounted to 27.9 g (98 mmol; 49%) of yellow crystals. Re-crystallization from methanol afforded pale yellow crystals, mp 165–167° C.

IR (KBr) 1651, 1549, 1450, 843 cm$^{-1}$ $^1$H NMR (CD$_3$CN) 3.54 (s, 6), 2.47 (s, 3), 2.18 (s, 6) ppm

EXAMPLE 7

Preparation of 1,3-Di-n-Propylimidazolium Hexafluorophosphate

Aqueous formaldehyde (37%) (8 ml, 0.10 mol)) was chilled in a 125 ml Erlenmeyer flask immersed in an ice-water bath. n-Propylamine (16.6 ml, 0.20 mol was added drop wise with stirring. Aqueous hexafluorophosphoric acid (60%) (15 ml, 0.10 mol) was added in small portions from a plastic syringe. Aqueous glyoxal (40%) (12 ml, 0.10 mol) was added drop wise and the mixture was allowed to stir overnight at room temperature yielding two liquid layers. The mixture was heated to 50° C. for 3 hours, and the lower layer separated and dried overnight on a rotary evaporator at 55° C. to give 18 g (62% yield) of a light orange liquid. Proton NMR showed that this hydrophobic salt is comprised of 1,3-di-n-propylimidazolium hexafluorophosphate, liquid at room temperature.

EXAMPLE 8

Preparation of a Mixture of 2:1:1 ratio of 1-n-Butyl-3-Ethylimidazolium, 1,3-Diethylimidazolium, and 1,3-Di-n-Butylnimdazolium Hexafluorophosphates Aqueous formaldehyde (37%) (15 ml, 0.20 mol)) was chilled in a 250 ml Erlenmeyer flask immersed in an ice-water bath. Aqueous ethylamine (16 ml, 0.20 mol) was added drop wise with stirring, followed by n-butylamine (20 ml, 0.20 mol). Aqueous hexafluorophosphoric acid (60%) (30 ml, 0.20 mol) was added in small portions from a plastic syringe. Finally, aqueous glyoxal (40%) (23 ml, 0.20 mol) was added drop wise and the mixture was allowed to stir for two days at room temperature yielding two liquid layers. The lower layer containing the dialkylated imidazolium salts was separated from the aqueous layer via a separatory funnel and washed with 100 ml of cold water affording 42 g of a faint yellow liquid (70% yield). Proton NMR confirmed the presence of a mixture of hydrophobic substituted imidazolium hexafluorophosphate salts, liquid at room temperature, incorporating a 2:1:1 ratio of 1-n-butyl-3-ethylimidazolium, 1,3-diethylimidazolium and 1,3-di-n-butyl hexafluorophosphates.

EXAMPLE 9

Preparation of a Mixture of 2:1:1 ratio of 1-n-Butyl-3-Methylimidazolium, 1,3-Dimethylimidazolium, and 1,3-Di-n-Butylimidazolium Hexafluorophosphates Aqueous formaldehyde (37%) (17.6 ml, 0.225 mol)) was chilled in a 250 ml Erlenmeyer flask immersed in an ice-water bath. n-Butylamine (22.5 ml, 0.225 mol was added drop wise with stirring, followed by aqueous methylamine (40%) (19.5 ml, 0.225 mol)). Aqueous hexafluorophosphoric acid (60%) (34 ml, 0.225 mol) was added in small portions from a plastic syringe. Aqueous glyoxal (40%) (27 ml, 0.225 mol) was added drop wise and the mixture was allowed to stir overnight at room temperature yielding two liquid phases. The mixture was heated to 50° C. overnight, cooled, and the lower layer separated and lyophilized to give 60 g (95% yield) of a light brown liquid. Proton NMR and mass spectrometry showed that this hydrophobic ionic liquid is comprised of a mixture of 2:1:1 ratio of 1-n-butyl-3-methylimidazolium, 1,3-dimethylimidazolium and 1,3-di-n-butyl hexafluorophosphates.

EXAMPLE 10

Preparation of a Mixture of a 5:1:4 Ratio of 1-n-Butyl-3-Methylimidazolium, 1,3-Dimethylimidazolium, and 1,3-Di-n-Butylimldazolium Hexafluorophosphates Aqueous formaldehyde (37%) (15.6 ml, 0.20 mol)) was chilled in a 250 ml Erlenmeyer flask immersed in an ice-water bath. n-Butylamine (22.5 ml, 0.225 mol was added drop wise with stirring, followed by aqueous methylamine (40%) (15.1 ml, 0.175 mol). Aqueous hexafluorophosphoric acid (60%) (30 ml, 0.20 mol) was added in small portions from a plastic syringe. Aqueous glyoxal (40%) (24 ml, 0.20 mol) was added drop wise and the mixture was allowed to stir overnight at room temperature-yielding two liquid layers. The mixture was heated to 50° C. overnight and the lower layer separated via a separatory funnel and dried on a rotary evaporator at 55° C. overnight to give 56 g (99% yield) of a light orange liquid. Proton NMR and mass spectrometry showed that this hydrophobic ionic liquid is comprised of a mixture of 5:4:1 ratio of 1-n-butyl-3-methylimidazolium, 1,3-dimethylimidazolium and 1,3-di-n-butyl hexafluorophosphates.

EXAMPLE 11

Ionic Conductivity and Viscosity

We have measured the room temperature conductivities and viscosities of 1-n-butyl-3-ethylimidazolium hexafluorophosphate ($BEIPF_6$), 1,3-Diethlyimidazolium hexafluorophosphate ($DEIPF_6$), and the 2:1:1 mixture of 1-n-butyl-3-ethylimidazolium, 1,3-diethyliridazolium and 1,3-di-n-butylimidazolium hexafluorophosphates. $BEIPF_6$ was prepared from 1-ethylimidazole, n-butylbromide (both from Aldrich) and $KPF_6$ (Strem), and purified in accordance with the multi-step route described in U.S. Pat. No. 5,827,602. $DEIPF_6$ (which is a solid at room temperature) was prepared from 1-ethylimidazole, ethylbromide (both from Aldrich) and $KPF_6$ (Strem), and purified in accordance with the multi-step route described in U.S. Pat. No. 5,827,602. We found that neat $BEIPF_6$ is twice as conductive as the 2:1:1 mixture as shown in Table 1. This finding is reasonable given that the viscosity data reveal that the 2:1:1 mixture is more than twice as viscous as the $BEIPF_6$.

We have also found, surprisingly, that a 2:1:1 mixture of 1-n-butyl-3-ethylimidazolium, 1,3-diethylimidazolium and 1,3-di-n-butylimidazolium hexafluorophosphates when dissolved in acetonitrile manifest higher room temperature conductivities than either $BEIPF_6$ or $DEIPF_6$ dissolved in acetonitrile (AN) alone (Table 1). This result is counterintuitive since one skilled in the art would expect that the 2:1:1 mixture (which comprises the large, poorly mobile 1,3-di-n-butylimidazolium cation) would be less conductive than a solution of the smaller diethylimidazolium and 1-n-butyl-3-ethylimidazolium cations dissolved in AN. Indeed, our viscosity measurements on samples of the 2:1:1 mixture, $DEIPF_6$, and $BEIPF_6$ dissolved in AN confirms this hypothesis: the viscosities of the 2.0M $BEIPF_6$ and 2.0M $DEIPF_6$ in AN are slightly lower than the viscosity of 2.0M 2:1:1 mixture in AN. This, in turn, implies that the ionic conductivities of the $BEIPF_6$/AN and $DEIPF_6$/AN solutions should be higher. We believe that there may be some synergistic solvation effects among the three polyalkylated imidazolium cations and the AN solvent that unexpectedly enhance the ionic conductivity of the solution.

TABLE 1

Specific Conductivities and Viscosities of Various Ionic Liquids at 22° C.

| Ionic Liquid | conductivity, mS/cm | viscosity, cP |
|---|---|---|
| 2:1:1 mixture (neat) | 1.6 | 251 |
| BEIPF$_6$ (neat) | 3.3 | 112 |
| 1.5 M 2:1:1 mixture/AN | 42.0 | — |
| 1.5 M BEIPF$_6$/AN | 41.0 | — |
| 2.0 M 2:1:1 mixture/AN | 43.0 | 1.4 |
| 2.0 M BEIPF$_6$/AN | 38.9 | 1.3 |
| 2.0 M DEIPF$_6$/AN | 41.4 | 1.2 |
| 3.0 M 2:1:1 mixture/AN | 25.9 | — |
| 3.0 M BEIPF$_6$/AN | 23.0 | — |

Because the sensitivity of the conductivity measurements was ±0.1 mS/cm, these data clearly demonstrate that one can achieve higher ionic conductivities over various concentrations by employing a mixture of hydrophobic ionic liquids instead of a single hydrophobic ionic liquid. Hydrophobic ionic liquid mixtures, when dissolved in a suitable solvent, would find use as high conductivity electrolytes in electrochemical power sources. Preferably these solvents are linear and cyclic organic carbonates, ethers, ketones, esters, formates, nitrites, nitro derivatives, amides, sulfones, sulfolanes, sulfonamides, partially halogenated hydrocarbons, polymers and combinations thereof.

EXAMPLE 12

Response to Microwave Radiation

Figure 1:
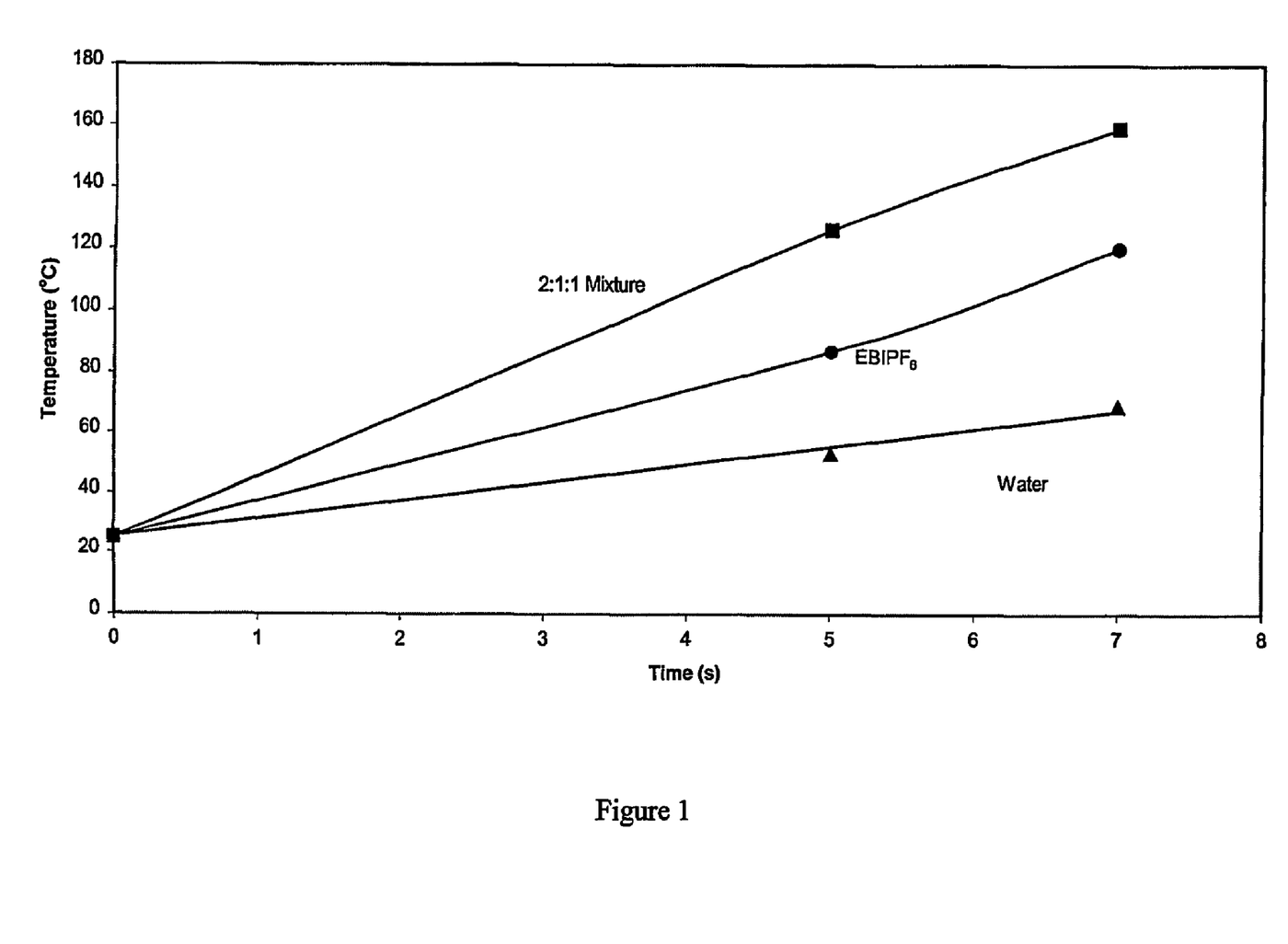
FIG. 1 shows a plot of the temperature of various neat ionic liquids irradiated with microwave energy as a function of time.

The thermal stability and lack of a vapor pressure make ionic liquids materials ideal for microwave assisted organic synthesis as described by Westman in WO 00/72956. We have found that a 2:1:1 mixture of 1-n-butyl-3-ethylimidazolium, 1,3-diethylimidazolium and 1,3-di-n-butylimidazolium hexafluorophosphates absorb microwave radiation at a faster rate than 1-n-butyl-3-ethylimidazolium hexafluorophosphate (EIPF$_6$) hydrophobic ionic liquid alone. Samples of 4 ml each of neat BEIPF$_6$, the neat 2:1:1 mixture, and water were subjected to microwave radiation provided by a small kitchen unit. The temperature of each sample was measured by a digital thermocouple as a function of various irradiation times. As shown in FIG. 1, after 7 seconds of irradiation the water warms up from room temperature to 65° C., while the 2:1:1 mixture reaches a temperature of 160° C. compared to 115° C. for the single BEIPF$_6$ ionic liquid. Therefore, the neat 2:1:1 mixture of three hydrophobic ionic liquids is a more efficient medium for the absorption of thermal energy induced by microwave radiation.

Figure 2:
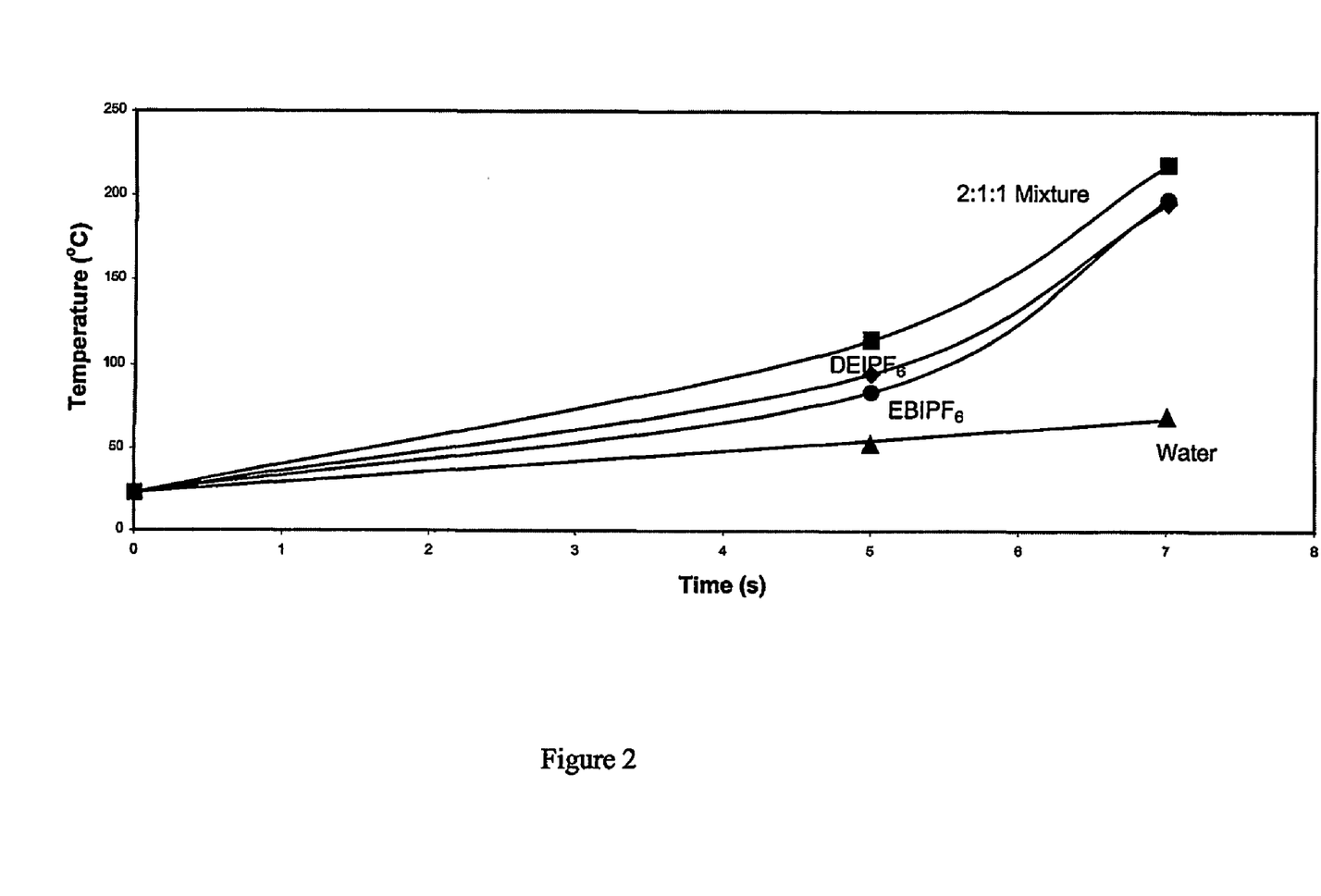
FIG. 2 shows a plot of the temperature of various ionic liquids dissolved in propylene carbonate and irradiated with microwave energy as a function of time.

We have also found that when a 2:1:1 mixture of 1-n-butyl-3-ethylimidazolium, 1,3-diethylimidazolium and 1,3-di-n-butylimidazolium hexafluorophosphates is dissolved in an organic solvent such as propylene carbonate, the mixture absorbs microwave radiation at a faster rate than either 1-n-butyl-3-ethylimidazolium hexafluorophosphate (BEIPF$_6$) or 1,3-diethylimidazolium hexafluorophosphate (DEIPF$_6$) dissolved alone in propylene carbonate (PC). FIG. 2 shows that the 2:1:1 mixture reaches a temperature of 220° C. after 7 seconds while the BEIPF$_6$ and BEIPF$_6$ reach a temperature of 195° C. Therefore, the 2:1:1 mixture of three hydrophobic ionic liquids dissolved in PC is a more efficient medium for the absorption of thermal energy induced by microwave radiation.

The improved rate of microwave absorption is observable both of the ionic liquids are used neat or if they are in solution. Solvents usable for these solutions are preferably organic solvents and include linear and cyclic organic carbonates, ethers, ketones, esters, formates, nitrites (particularly acetonitrile), nitro derivatives, amides, sulfones, sulfolanes, sulfonamides, partially halogenated hydrocarbons, polymers and combinations thereof.

Those with expertise in this technology will recognize variations that are consistent with the disclosure herein.

What is claimed is:

1. A process for making one or more hydrophobic ionic salts of the structure wherein $R_1$ and $R_3$ each is an alkyl moiety, each of $R_2$, $R_4$, and $R_5$ is hydrogen or said alkyl moiety, and $X^-$ is an anion, selected from the group consisting of polyatomic inorganic and polyatomic organic anions, said process comprising the steps of:
 a. mixing an aldehyde having either hydrogen or alkyl group substituents with one or more alkyl amines comprising an alkyl moiety desired for said hydrophobic ionic salts to form a mixture;
 b. adding the acid form of one or more anions desired for said hydrophobic ionic salts to said mixture;
 c. adding an aqueous solution of an alpha-dicarbonyl compound to said mixture;
 d. allowing the components of said mixture to react; and
 e. separating said hydrophobic ionic salts from said mixture.

2. The process of claim 1 wherein said hydrophobic ionic salts are ionic liquids.

3. The process of claim 2 wherein a single hydrophobic ionic liquid is made.

4. The process of claim 2 wherein two or more hydrophobic ionic liquids are made.

5. The process of claim 4 wherein said hydrophobid ionic liquids have improved ionic conductivity.

6. The process of claim 4 wherein said hydrophobic ionic liquids have improved absorption of microwave energy.

7. The process of claim 1 wherein said alkyl moieties are the same.

8. The process of claim 1 wherein said alkyl moieties are different.

9. The process of claim 8 wherein at least one of said alkyl moieties comprises 4 to 10 carbon atoms.

10. The process of claim 1 wherein said anion is selected from the group consisting of $PF_6^-$, $AsF_6^-$, $SbF_6^-$, $C_nF_{2n+1}CO_2$, $C_nF_{2n+1}SO_3^-$, where n=1 to 10 carbon atoms in either straight or branched chains; $(C_nF_{2n+1}SO_2)_2N^-$, $(C_nF_{2n+1}SO_2)_3C^-$, where n=1 to 5 carbon atoms in either straight or branched chains; and $(C_nF_{2n+1})PF_5^-$, $(C_nF_{2n+1})_2PF_4^-$, $(C_nF_{2n+1})_3PF_3^-$, and $(C_nF_{2n+1})_4PF_2^-$, where n=1 to 5 carbon atoms in either straight or branched chains.

11. The process of claim 10 wherein said anion is $PF_6^-$.

12. The process of claim 1 wherein, in step (a), said alkyl amines are one or more $C_{1-20}$ alkyl amines, where $C_{1-20}$ alkyl is a linear, cyclic or branched hydrocarbon group having from 1 to 20 carbon atoms.

13. The process of claim 12 wherein the alkyl moieties of said alkyl amines are selected from the group consisting of methyl, ethyl, n-propyl, iso-propyl, cyclopropyl, n-butyl, sec-butyl, t-butyl, cyclobutyl, pentyl, cyclopentyl, hexadecyl, heptadecyl, octadecyl and nonadecyl.

14. The process of claim 2 wherein, in step (a), said alkyl amines are one or more $C_{1-20}$ alkyl amines, where $C_{1-20}$ alkyl is a linear, cyclic or branched hydrocarbon group having from 1 to 20 carbon atoms.

15. The process of claim 14 wherein the alkyl moieties of said alkyl amines are selected from the group consisting of methyl, ethyl, n-propyl, iso-propyl, cyclopropyl, n-butyl, sec-butyl, t-butyl, cyclobutyl, pentyl, cyclopentyl, hexadecyl, heptadecyl, octadecyl and nonadecyl.

16. The process of claim 1, wherein, in step (a), said alkyl group substituents comprise from 1 to 10 carbon atoms.

17. The process of claim 16, wherein, in step (a), said aldehyde is aqueous formaldehyde.

18. The process of claim 17, wherein, in step (a), said aldehyde is acetaldehyde.

\* \* \* \* \*

UNITED STATES PATENT AND TRADEMARK OFFICE
CERTIFICATE OF CORRECTION

| | |
|---|---|
| PATENT NO. | : 7,253,289 B2 |
| APPLICATION NO. | : 10/250801 |
| DATED | : August 7, 2007 |
| INVENTOR(S) | : Rex Xiaofeng Ren et al. |

It is certified that error appears in the above-identified patent and that said Letters Patent is hereby corrected as shown below:

On the Title page, please insert:
--Related U.S. Application Data
(60) Provisional Application No. 60/262,661, filed on Jan. 22, 2001.--;

Abstract, line 10, "methylanune" should read --methylamine--;

Abstract, line 15, "isopropylaine" should read --iso-propylamine--;

Abstract, line 15, "isbutyl" should read --iso-butyl--;

Abstract, line 18, "bis (perfluoroalkylsulfony-prnide" should read --bis (perfluoroalkyl-sulfony) imide--;

Column 1, line 23, "polyatoniic" should read --polyatomic--;

Column 1, line 40, "haloaluniinate" should read --haloaluminate--;

Column 7, line 4, "spontaine" should read --spontane--;

Column 8, line 42, "Pentamethylnimdazolium" should read --Pentamethylimidazolium--;

Column 9, line 26, "Butylnimdazolium" should read --Butylimidazolium--;

Column 10, line 2, "dimethylirnidazolium" should read --dimethylimidazolium--;

Column 10, line 10, "Butylimldazolium" should read --Butylimidazolium--;

Column 10, line 38, "diethyliridazolium" should read --diethylimidazolium--;

UNITED STATES PATENT AND TRADEMARK OFFICE
CERTIFICATE OF CORRECTION

PATENT NO. : 7,253,289 B2
APPLICATION NO. : 10/250801
DATED : August 7, 2007
INVENTOR(S) : Rex Xiaofeng Ren et al.

It is certified that error appears in the above-identified patent and that said Letters Patent is hereby corrected as shown below:

Column 11, line 48, "$(EIPF_6)$" should read --$(BEIPE_6)$--;

Column 12, claim 5, line 50, "hydrophobid" should read --hydrophic--.

Signed and Sealed this

Ninth Day of June, 2009

JOHN DOLL
*Acting Director of the United States Patent and Trademark Office*

UNITED STATES PATENT AND TRADEMARK OFFICE
CERTIFICATE OF CORRECTION

PATENT NO. : 7,253,289 B2  
APPLICATION NO. : 10/250801  
DATED : August 7, 2007  
INVENTOR(S) : Rex Xiaofeng Ren et al.

It is certified that error appears in the above-identified patent and that said Letters Patent is hereby corrected as shown below:

On the Title page, please insert:
--Related U.S. Application Data
(60) Provisional Application No. 60/262,661, filed on Jan. 22, 2001.--;

Abstract, line 10, "methylanune" should read --methylamine--;

Abstract, line 15, "isopropylaine" should read --iso-propylamine--;

Abstract, line 15, "isbutyl" should read --iso-butyl--;

Abstract, line 18, "bis (perfluoroalkylsulfony-prnide" should read --bis (perfluoroalkyl-sulfony) imide--;

Column 1, line 23, "polyatoniic" should read --polyatomic--;

Column 1, line 40, "haloaluniinate" should read --haloaluminate--;

Column 7, line 4, "spontaine" should read --spontane--;

Column 8, line 42, "Pentamethylnimdazolium" should read --Pentamethylimidazolium--;

Column 9, line 26, "Butylnimdazolium" should read --Butylimidazolium--;

Column 10, line 2, "dimethylirnidazolium" should read --dimethylimidazolium--;

Column 10, line 10, "Butylimldazolium" should read --Butylimidazolium--;

Column 10, line 38, "diethyliridazolium" should read --diethylimidazolium--;

UNITED STATES PATENT AND TRADEMARK OFFICE
CERTIFICATE OF CORRECTION

PATENT NO. : 7,253,289 B2
APPLICATION NO. : 10/250801
DATED : August 7, 2007
INVENTOR(S) : Rex Xiaofeng Ren et al.

It is certified that error appears in the above-identified patent and that said Letters Patent is hereby corrected as shown below:

Column 11, line 48, "($EIPF_6$)" should read --($BEIPE_6$)--;

Column 12, claim 5, line 50, "hydrophobid" should read --hydrophic--.

Column 12, claim 10, line 61, "$_1CO_2$," should read --$_1CO_2^-$,--.

This certificate supersedes the Certificate of Correction issued June 9, 2009.

Signed and Sealed this

Eighth Day of September, 2009

David J. Kappos
*Director of the United States Patent and Trademark Office*